United States Patent [19]

Litton

[11] Patent Number: 4,573,459

[45] Date of Patent: Mar. 4, 1986

[54] THUMB AND FINGER EXTENSION DEVICE

[76] Inventor: Bruce W. Litton, 9533 Shiloh Wood Ct., Indianapolis, Ind. 46234

[21] Appl. No.: 526,475

[22] Filed: Aug. 25, 1983

[51] Int. Cl.$^4$ ............................................. A61F 5/04
[52] U.S. Cl. .............................. 128/92 A; 128/84 R; 128/92 G
[58] Field of Search ................ 128/92 A, 92 R, 92 G, 128/84 R, 84 B, 84 C

[56] References Cited

U.S. PATENT DOCUMENTS

| | | | |
|---|---|---|---|
| 2,002,021 | 5/1935 | Rouse | 128/84 R |
| 2,185,322 | 1/1940 | Anderson | 128/92 A |
| 2,204,266 | 6/1940 | Wilcox | 128/92 A |
| 2,237,251 | 4/1941 | Longfellow | 128/84 C |
| 2,247,187 | 6/1941 | Cunningham | 128/84 R |
| 2,371,519 | 3/1945 | Haynes | 128/92 A |
| 2,434,431 | 1/1948 | Pincock | 128/92 A |
| 3,583,397 | 6/1971 | Baddour | 128/84 C |
| 3,709,219 | 1/1973 | Halloran | 128/92 A |
| 3,809,075 | 5/1974 | Matles | 128/92 A |
| 3,900,025 | 8/1975 | Barnes, Jr. | 128/84 R |
| 4,006,740 | 2/1977 | Volkov et al. | 128/84 B |
| 4,159,716 | 7/1979 | Borchers | 128/92 A |
| 4,187,841 | 2/1980 | Kautson | 128/92 A |
| 4,220,146 | 9/1980 | Cloutier | 128/84 B |

FOREIGN PATENT DOCUMENTS 387700 9/1973 U.S.S.R. ............................ 128/92 A

Primary Examiner—Robert Peshock
Assistant Examiner—C. W. Shedd
Attorney, Agent, or Firm—Woodard, Weikart, Emhardt & Naughton

[57] ABSTRACT

A device for extending a phalangeal bone in the thumb or one of the fingers of a hand. The device includes proximal and distal pairs of bone pins, a pair of screw threaded bars for adjusting the distance between the pairs of bone pins, first and second pairs of guide posts and four pairs of pin retaining members. The guide posts and pin retaining members retain the bone pins in relative alignment as the thumb or finger is progressively extended by adjustment of the bars. Each bar is laterally offset from the corresponding pair of guide posts, while each pair of guide posts is symmetrically positioned relative to the bone pins. The device further includes a brass bushing press fit within each of the apertures which serves to maintain accurate alignment of the bone pins as the thumb or finger is extended. A retaining clip is removably attached at one end of each of the guide posts. Each bar includes a rectangular head for turning the bars and a measuring block medially positioned along the length thereof to assist in measuring the amount of thumb or finger extension.

9 Claims, 4 Drawing Figures

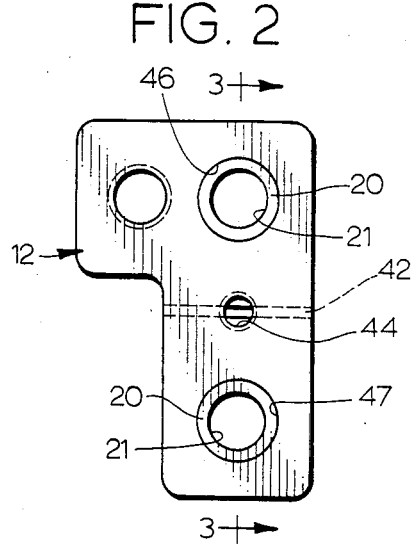
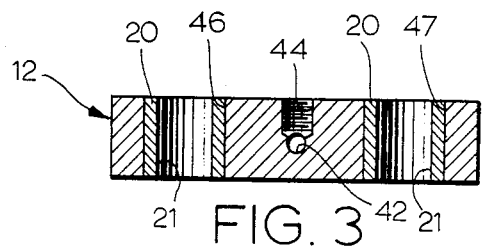
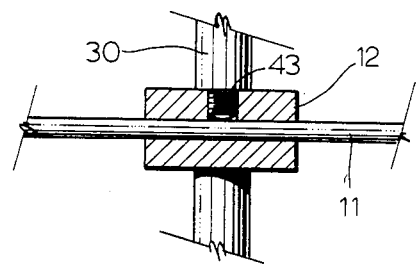

THUMB AND FINGER EXTENSION DEVICE

BACKGROUND OF THE INVENTION

The present invention relates generally to extension devices for bones and, more particularly, to those devices which are especially suited for extending a phalangeal bone in the thumb or finger of a hand.

From time to time in reconstructive hand surgery, including the problems with the congenital anomalies of the hand and following certain trauma, it becomes desirable to lengthen the thumb and/or one or more fingers of the hand. More specifically, such techniques are applicable for children, both with rudimentary phalanges or shortened segments of their hand, and to adults who have partially lost their thumb but still retain the first metacarpal. The method of lengthening involves an osteotomy followed by the application of an apparatus which provides a very gradual separation of the divided bone ends, thereby adding considerable length to the specific body part. Such procedures are particularly beneficial following thumb loss in that as much as 2-3 additional centimeters of thumb length may be gained by dividing and separating the first metacarpal and subsequently interposing a bone graft; the end result being a considerably more functional thumb unit possessing an ability to pinch and grasp which was not present prior to the operation.

To this end, various devices have been designed which attach to pins driven through the bones following bone division and allow the patient to gradually distract the bony units over a period of time commensurate with the patient's discomfort and the ability of the patient's skin and soft tissues to stretch. Unfortunately, none of these devices have proved totally satisfactory in that their designs exhibit disadvantages from one point of view or another. Thus, problems with bending, jamming, corrosion, and failure to turn have been frequent. Some of these problems have resulted in a failure of the extension procedure, infection, or an inability to obtain the desired amount of bone separation.

The following patent references disclose bone extension and compression devices of a type which are generally relevant to the present invention:

| U.S. Pat. No. | Inventor | Issued |
| --- | --- | --- |
| 2,002,021 | Rouse | May 21, 1935 |
| 4,159,716 | Borchers | July 3, 1979 |
| 4,187,841 | Knutson | Feb. 12, 1980 |
| 3,709,219 | Halloran | Jan. 9, 1973 |
| 3,900,025 | Barnes, Jr. | Aug. 19, 1975 |
| 2,371,519 | Haynes | Mar. 13, 1945 |

U.S. Pat. No. 2,002,021 to Rouse discloses a surgical fraction extension appliance designed to apply stretching or extension to the limbs, for the purpose of adjusting the fractured ends of bones in the arms or legs preparatory to the application of splice plates or similar devices to the meeting ends of the fractured bone.

U.S. Pat. No. 4,149,716 to Borchers discloses an apparatus which is apparently useful for the compression and realignment of bone structures, particularly in the correction of splay foot deformity. The apparatus discloses a U-shaped jig having axially aligned threaded and unthreaded apertures, a threaded adjustment screw engaged in the threaded aperture, and a bushing having a threaded axial passage therethrough slidably disposed in the unthreaded aperture. A threaded drill pin is engaged in the passage of the bushing and serves to pierce and traverse the boned structures and hold them in a desired position of alignment.

U.S. Pat. No. 4,187,841 to Knutson discloses a surgical tool which is apparently utilized for either compression or distraction of a fractured bone. The tool includes a threaded shaft having a pair of cap members one of which includes a short pin projecting therefrom into the bone. A second pin projects from an internally threaded sleeve which is movably mounted on the shaft between the cap members. The threaded shaft is positioned parallel with the length of the bone during use.

U.S. Pat. No. 3,709,219 to Halloran discloses a bone compression device including two arms each having a pin mounted thereon at one end. Two pairs of couplings are rotatably mounted on the arms in spaced a space apart relationship. A pair of externally threaded tightening rods are engaged in the pairs of couplings and effect relative movement of the pins by screw movement. The use of guide posts slidably mounted in aligned apertures is not disclosed.

U.S. Pat. No. 3,900,025 to Barnes, Jr. discloses an apparatus for selectively distracting or compressing contiguous longitudinal bone segments. The apparatus includes two support members each positioned longitudinally coextensively adjacent respective bone segments. The members include internally threaded and axially aligned apertures which engage an externally threaded driving rod. The apparatus further discloses the use of a single guiding rod slidably received through a second pair of aligned apertures. The guiding rod apertures are laterally spaced from the threaded apertures such that the guiding rod and driving rod are positioned on opposite sides of bone pins projecting from each member.

The closest art of which the inventor is aware, and upon which the present invention is a distinct improvement, discloses a thumb or finger stretching device having pairs of pins, each of which extend laterally through a separate pair of plates disposed on both sides of the thumb or finger being stretched. The pairs of plates are also arranged longitudinally such that a single guide rod extends through aligned apertures in each column of plates. An elongate screw also extends through each column of plates such that each screw and corresponding guide rod are symmetrically positioned relative to the pins. Further details of construction involve providing the guide rods with bolt stops at each end, providing the screws with hexagonal shaped heads for turning, and forming the plates and rods of a metal which exhibits corrosion problems. The performance of this device has been unsatisfactory, however, in that the device exhibits the bending, jamming and corrosion problems previously mentioned.

SUMMARY OF THE INVENTION

A device for extending a phalangeal bone in one of the fingers or the thumb of the hand, according to one embodiment of the present invention, is characterized by a plurality of proximal and distal bone pins, a means for adjusting the distance between the proximal and distal bone pins, and a pin retaining means. The pin retaining means is characterized by first and second pairs of guide posts and at least four pairs of pin retaining members. Each pair of pin retaining members is adapted for attachment to a different one of the bone pins on opposite sides of the thumb or finger being extended. Each pin retaining member defines a pair of apertures, the pairs of apertures being separately longitudinally aligned for receiving therethrough a different one of the guide posts. Each of the pairs of guide posts is symmetrically positioned relative to the bone pins with the adjusting means laterally offset therefrom. The pin retaining means serves to retain the bone pins in relative alignment as the thumb or finger is progressively extended by the device.

It is an object of the present invention to provide an improved device for extending the thumb or fingers of the hand.

Related objects and advantages of the present invention will become more apparent by reference to the following figures and detailed description.

BRIEF DESCRIPTION OF THE DRAWINGS

FIG. 2 is a top plan view of one of the pin retaining plates.

FIG. 3 is a section view of the pin retaining plate of FIG. 2 taken along lines 3—3.

FIG. 4 is an enlarged fragmentary section view taken along lines 4—4 in FIG. 1.

DESCRIPTION OF THE PREFERRED EMBODIMENT

Figure 1:
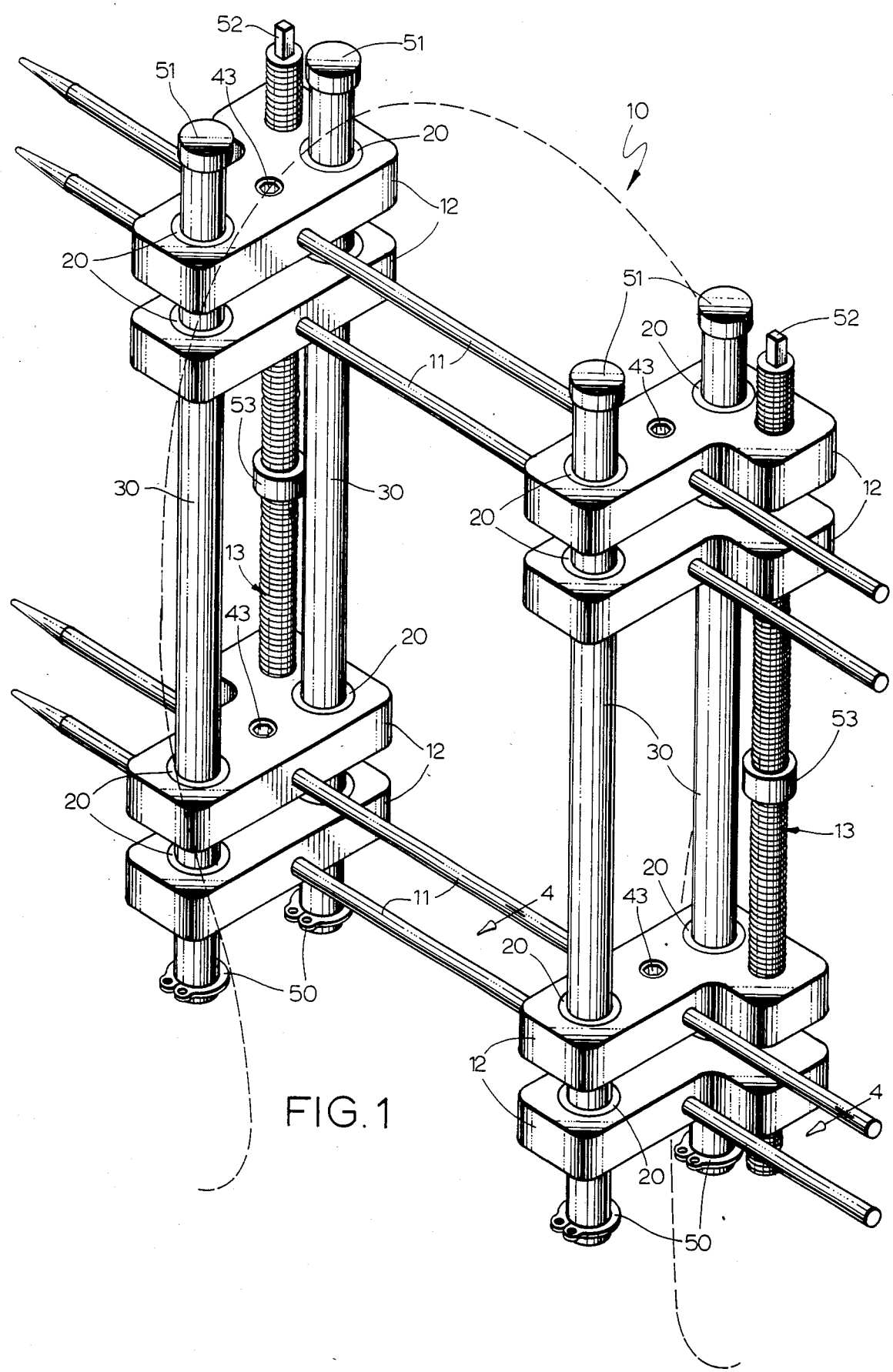
FIG. 1 is a perspective view of the preferred embodiment of the thumb and finger extension device of the present invention with a thumb in position for extension shown in phantom lines.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to the drawings in detail, the preferred embodiment of the device of the present invention is generally designated at 10. The device 10 comprises proximal and distal pairs of bone pins 11 each of which is received through a pair of horizontally aligned apertures in pin retaining plates 12. A pair of adjustment bars 13 are received through vertically aligned apertures in plates 12 which are internally threaded for engagement with external threads on adjustment bars 13. A pair of bushings 20 are mounted within a pair of corresponding apertures in each of the plates 12, and contain apertures through which a pair of guide posts 30 are slidably received. Plates 12, bushings 20, and guide posts 30 together serve to retain bone pins 11 in relative alignment as the thumb or finger is progressively extended by turning adjustment bars 13.

Each of the bone pins 11 are adapted to pierce laterally through the thumb or finger of a patient, such as is shown in phantom in FIG. 1, with the respective pairs of proximal and distal pins 11 secured to adjacent divided segments of the bone to be extended. Bone pins 11 are identically formed and made of stainless steel.

Referring to FIGS. 2-4, details of contruction of one of the plates 12 is more fully shown. It is to be understood that each of the plates 12 are structurally similar, and except for those differences noted herein, a description of one suffices to describe the details of each. Plate 12 has a horizontal aperture 42 sized to receive therethrough bone pin 11. A set screw 43 engages pin 11 through internally threaded aperture 44 so as to lock the position of pin 11 in aperture 42. It is to be noted that the position of set screw 43 in adjacent plates 12 is reversed to facilitate access thereto. Vertical apertures 46 and 47 are sized to receive therein a pair of cylindrically shaped brass bushings 20 in a press fit arrangement. Bushings 20 contain an aperture 21 which is sized for a slip fit with guide posts 30. Bushings 20 are an important feature of the invention in that they serve to maintain accurate alignment of the bone pins as the thumb or finger is progressively extended by turning bars 13. Aperture 48 is internally threaded for engagement with the external threads of adjustment bar 13. It is particularly noted that apertures 46 and 47 are symmetrically positioned relative to aperture 42, and aperture 48 is laterally offset from apertures 46 and 47 in a position of longitudinal alignment with aperture 46. This arrangement permits the proximal and distal pairs of bone pins 11 to be relatively moved apart without the device 10 exhibiting the jamming and bending problems encountered by previous devices used for this purpose. Plates 12 are made from stainless steel.

Guide posts 30 are identically formed, thus a description of one suffices to describe each. Guide post 30 is made from stainless steel and, as previously mentioned, is sized for a slip fit inside bushings 20. A retaining clip 50 is removably attached at one end of guide post 30, while the other end has a cylindrical head 51.

Bars 13 are identically formed, thus a description of one suffices to describe both. Bar 13 is oppositely threaded along its upper and lower halves to permit the distance between the proximal and distal pairs of bone pins 11 to be increased or decreased by screw engagement with the internally threaded apertures 48 corresponding to plates 12. Of course, the apertures 48 corresponding to those plates 12 which retain the proximal pair of bone pins 11 is also oppositely threaded from the apertures 48 corresponding to those plates 12 retaining the distal pair of bone pins 11. Bar 13 includes a head 52 at one end having a rectangular lateral cross section which permits bar 13 to be turned by a socket wrench tool. Bar 13 further includes a measuring block 53 medially positioned along the length thereof to assist in measuring the progressive extension of the thumb or finger.

The manner in which device 10 is used to extend a thumb or finger may be described as follows. The bone to be extended is first surgically divided into two segments. The proximal and distal pairs of bone pins are then inserted through appropriately located holes drilled in the divided bone segments. Plates 12 are then secured to bone pins 11 on both sides of the thumb or finger, using set screws 43 to lock the position of plates 12 on pins 11. Adjustment bars 13 are then turned to separate the divided bone segments. The thumb or finger is progressively stretched or extended by periodically turning adjustment bars 13 until the desired amount of bone extension is achieved.

While the invention has been illustrated and described in detail in the drawings and foregoing description, the same is to be considered as illustrative and not restrictive to character, it being understood that only the preferred embodiment has been shown and described and that all changes and modifications that come within the spirit of the invention are desired to be protected.

What is claimed is:

1. An extension device for extension of a digit, such as a thumb or finger, comprising:
   a plurality of proximal bone pins adapted to extend laterally through a first one of two separated bone segments in a digit to be extended longitudinally;
   a plurality of distal bone pins adapted to extend laterally through the other one of said two separated bone segements;
   means for progressively extending the distance between said proximal and distal bone pins;
   means for maintaining said proximal and distal bone pins in relative alignment as said digit is progressively extended by operation of said extending means, said maintaining means including
   a pin retaining member corresponding to each of said bone pins, each said pin retaining member receiving a different one of said bone pins, and
   a pair of guide posts slidably received through each of said pin retaining members, said guide being positioned on opposite sides of said bone pins; and generally aligned with the direction of extension of said digit; and said extending means being laterally offset from said guide posts.

2. The extension device of claim 1 wherein said extending means includes an elongate bar having oppositely threaded first and second portions threadedly received within said pin retaining members respectively corresponding to said proximal and distal bone pins, said elongate bar thereby permitting the distance between said proximal bone pins and said distal bone pins to be varied by screw movement.

3. The extension device of claim 2 wherein said elongate bar is parallel to both of said guide posts.

4. The extension device of claim 3 wherein all of said bone pins are parallel to one another.

5. The extension device of claim 4 wherein said bone pins are each perpendicular to the plane of said pair of guide posts.

6. The extension device of claim 5 wherein said elongate bar includes a measuring block medially positioned along the length thereto to assist in measuring the progressive extension of said digit.

7. The extension device of claim 6 wherein said pin retaining members and said guide posts are made of stainless steel.

8. The extension device of claim 1 which incorporates similar structures on opposite sides of the digit being extended by comprising:
   said maintaining means including a pair of pin retaining members corresponding to each of said bone pins, each said pair of pin retaining members being positioned on opposite sides of said digit being extended and forming an associated set of pin retaining members on each side; a pair of guide posts slidably received through each associated set of pin retaining members on opposite sides of the digit being extended, the guide posts of a corresponding pair being symmetrically positioned relative to said bone pins, said extending means including a pair of elongate bars, each said elongate bar corresponding to and laterally offset from a different pair of guide posts.

9. The extension device of claims 1 or 8 wherein each of said pin retaining members includes at least one guide bushing defining an aperture through which one of said guide posts is slidably received, said aperture in said guide bushing being closely sized relative to said guide post to maintain accurate alignment of said bone pins as said digit is progressively extended.

* * * * *